(12) United States Patent  
Koike

(10) Patent No.: US 9,220,629 B2  
(45) Date of Patent: Dec. 29, 2015

(54) WEARABLE AIRWAY SUPPORTING DEVICE

(76) Inventor: Hideo Koike, White Plains, NY (US)

( * ) Notice: Subject to any disclaimer, the term of this patent is extended or adjusted under 35 U.S.C. 154(b) by 409 days.

(21) Appl. No.: 13/406,089

(22) Filed: Feb. 27, 2012

(65) Prior Publication Data

US 2013/0220339 A1   Aug. 29, 2013

(51) Int. Cl.
*A61F 5/56*   (2006.01)

(52) U.S. Cl.
CPC ........................................ *A61F 5/56* (2013.01)

(58) Field of Classification Search
USPC ............... 128/848, 859–862, 201.22–201.24, 128/201.14, 201.29; 602/902, 74; 433/6–7; 606/204.25, 199
See application file for complete search history.

(56) References Cited

U.S. PATENT DOCUMENTS

| 6,918,394 | B2 | 7/2005 | Matsuda et al. |
| 6,981,503 | B1 | 1/2006 | Shapiro |
| 7,331,349 | B2 | 2/2008 | Brady et al. |
| 2004/0187873 | A1 | 9/2004 | Brown |
| 2007/0181135 | A1 | 8/2007 | Baker |
| 2008/0173313 | A1 | 7/2008 | Brady et al. |
| 2010/0062391 | A1* | 3/2010 | King et al. ...................... 433/140 |
| 2011/0296584 | A1* | 12/2011 | Kuo .................................... 2/206 |
| 2011/0308528 | A1* | 12/2011 | Ciardullo ....................... 128/848 |
| 2012/0186591 | A1* | 7/2012 | Sethi et al. .................... 128/859 |

FOREIGN PATENT DOCUMENTS

| JP | 2002-011032 A | 1/2002 |
| JP | 2006-328616 A | 12/2006 |
| JP | 2007-068949 A | 3/2007 |
| JP | 2011-083314 A | 4/2011 |
| WO | WO 2007/049836 A | 5/2007 |

* cited by examiner

*Primary Examiner* — Ophelia A Hawthorne
(74) *Attorney, Agent, or Firm* — Robert Gorman; Gorman Law Offices

(57) ABSTRACT

A wearable airway supporting device consisting essentially of elastic textile products and a matching set of form-fit mandible projectors, and has portions that encircle the head such that, when combined with a set of form-fit mandible projectors, exert pressure on at least the pterygoideus internus section of the user's mandible so as to apply upwardly, outward pressure on the lower jaw (mandible) in order to stabilize the same while the user is sleeping or unconscious, thereby preventing snoring, obstructive sleep apnea, and other airway obstruction caused by the tongue dropping back into the throat and blocking the user's airway. When the elastic members are placed around the front and back of the user's head, the device keeps the user's mandible jutted forward and prevents the tongue from falling back so that air flows through his airway.

8 Claims, 7 Drawing Sheets

WEARABLE AIRWAY SUPPORTING DEVICE

BACKGROUND OF THE INVENTION

In general, the present invention relates to devices for treating upper airway obstruction problems, particularly some forms of obstructive sleep apnea and snoring, as well as applications in clinical settings, such as those involving the administration of anesthesia. Upper airway obstruction is a natural phenomenon in human beings that may manifest itself physiologically in different ways, such as in snoring while sleeping and/or pathologically through phenomena such as obstructive sleep apnea (OSA) and furthermore, may also manifest itself under certain clinical situations, such as anesthesia or induced sedation.

Approaches to maintain the integrity of the airway in order to avoid upper airway obstruction have included, in clinical settings, endotracheal intubation, introduction of nasal or oral airways, use of LMA (laryngeal mask airway) devices, and manual maneuvers such as chin lift and jaw thrust, such as those disclosed in U.S. Pat. Nos. 6,918,394, 6,981,503, PCT Pat. Pub. No. WO 2007/049836, and US Pat. Pub. Nos. 2004/018783 and 2007/0181135, each of which is hereby incorporated by reference in their entirety. However, endotracheal intubation, LMA, and oral/nasal airway placement approaches are too invasive to be applied to conscious patients. Chin lift and jaw thrust devices may require another person to perform and not be always available. In non-clinical settings, continuous positive air pressure (C-PAP) applications and jaw supporters have been proposed. Frequently, the jaw supporters are not wearable, or are such that they utilize adjustable straps and the like that overlap each other and create unnecessary pressure and discomfort to the users face and head in overlapping areas, or are otherwise uncomfortable to wear. Even worse, the approaches to wearable jaw supporters tend to involve straps that clamp the lower jaw shut or pull the lower jaw tight towards the base of the skull, in an inwardly tensioned direction. Approaches to clamping the jaw shut, or alternatively, to pulling the jaw back towards the base of the skull in an inwardly-tensioned fashion, do not provide the most comfortable solution for the problems at hand, and moreover may provide an equally bad obstruction in the breathing of some patients.

Alternative approaches, such as C-PAP have gained in popularity as a treatment of OSA, especially with morbidly obese people. However, this approach is cumbersome because, in addition to being expensive, the mask of the C-PAP is bulky and unpleasant to wear, and furthermore is noisy because of the machine operation necessarily associated therewith. Other treatment options for OSA may relate to use of a mouth piece, however, this requires the mouth piece needs to be individually made by a dentist or oral surgical specialist based on the oral anatomy of the person. Moreover, this approach is also time consuming, expensive, and generally unpleasant for the patient, given that he must necessarily sleep with the mouthpiece in his mouth. Hence, there is a need for a new non-invasive approach to supporting the airway of patient or user that can be applied for a treatment of OSA, snoring, and which can also be used to keep the airways open during the course of administration of anesthesia and sedation, but does so in such a way so as to provide much-needed comfort of wear, while still overcoming the structural deficiencies of otherwise cumbersome jaw thrusters and other treatments.

BRIEF SUMMARY OF THE INVENTION

The device of the present invention will normally be employed by sleeping individuals in order to prevent or reduce OSA, or employed by medical professionals for use on anesthetized patients during procedures under sedation or anesthesia, but will do so in such a way as to provide for a more maximized, yet comfortable jaw thrust that can be easily used and worn by subjects. Because previous attempts were not provided with any aspects of comfort or wearability, embodiments of the present invention overcome such limitations and further provide for the usage of breathable, washable materials, that offer the advantage of being readily usable ongoing usage in sterile operating environments, as well as being hygienically predisposed for ongoing use by patients during recurring sleep sessions. To this end, the present event invention is a simple mask made of comfortable, washable materials that can easily fit around a human head in such a way so as to provide an effective jaw thrust in a outward (rather than inward) fashion that will not only afford a comfortable structure for ease of ongoing usage, but will vastly improve the maintenance of an opened mouth position which limits tongue droppage into the back of the throat.

The device of the invention is therefore a wearable airway supporting device that supports the lower jaw of a human and is designed to satisfy the aforementioned needs for reducing snoring, obstructive sleep apnea, and airway obstruction during activities involving sedation or anesthesia administration. To this end, the wearable airway supporting device is comfortable, hygienic, ease to use, and supports the lower jaw by exerting a supporting force in an outward direction away from the skull of a patient. In doing so, the supporting device applies pressure on the lower jaw which prevents the user's mouth from slackening backwards in a position that would cause airway obstruction problems such as the tongue dropping back into the throat during periods of sleep or unconsciousness. The wearable airway supporting device is made of fabrics and materials that stretch and conform to the users unique head shape and size. In one embodiment, the wearable airway supporting device includes a comfortable one-piece fabric (such as polyester, acrylic, polychloroprene, elastane, etc.) that is inherently elastic, or which has an elastic design incorporated therein, and is shaped so as to fit around the upper jaw area of the face and around the skull of a human to overcome the aforementioned airway obstruction problems. The wearable airway supporting device keeps the lower jaw thrusted outwards from the skull during the sleep state or unconsciousness when airway obstruction commonly occurs. While awake, the supporter allows the user to breathe through the mouth talk eat, drink or cough. The elasticity of the supporter, and the various different sizes that can be made, allows a user, with any head circumference and any shape jaw to use it comfortably. The supporter has no projecting structures on any side of the head that can cause the user discomfort while sleeping. Unlike prior methods, the present invention tends to stay on the head of the user while sleeping or in an unconscious state, and does not interfere with either sleep or medical procedures for patients under sedation.

DETAILED DESCRIPTION OF THE INVENTION

Figure 1:
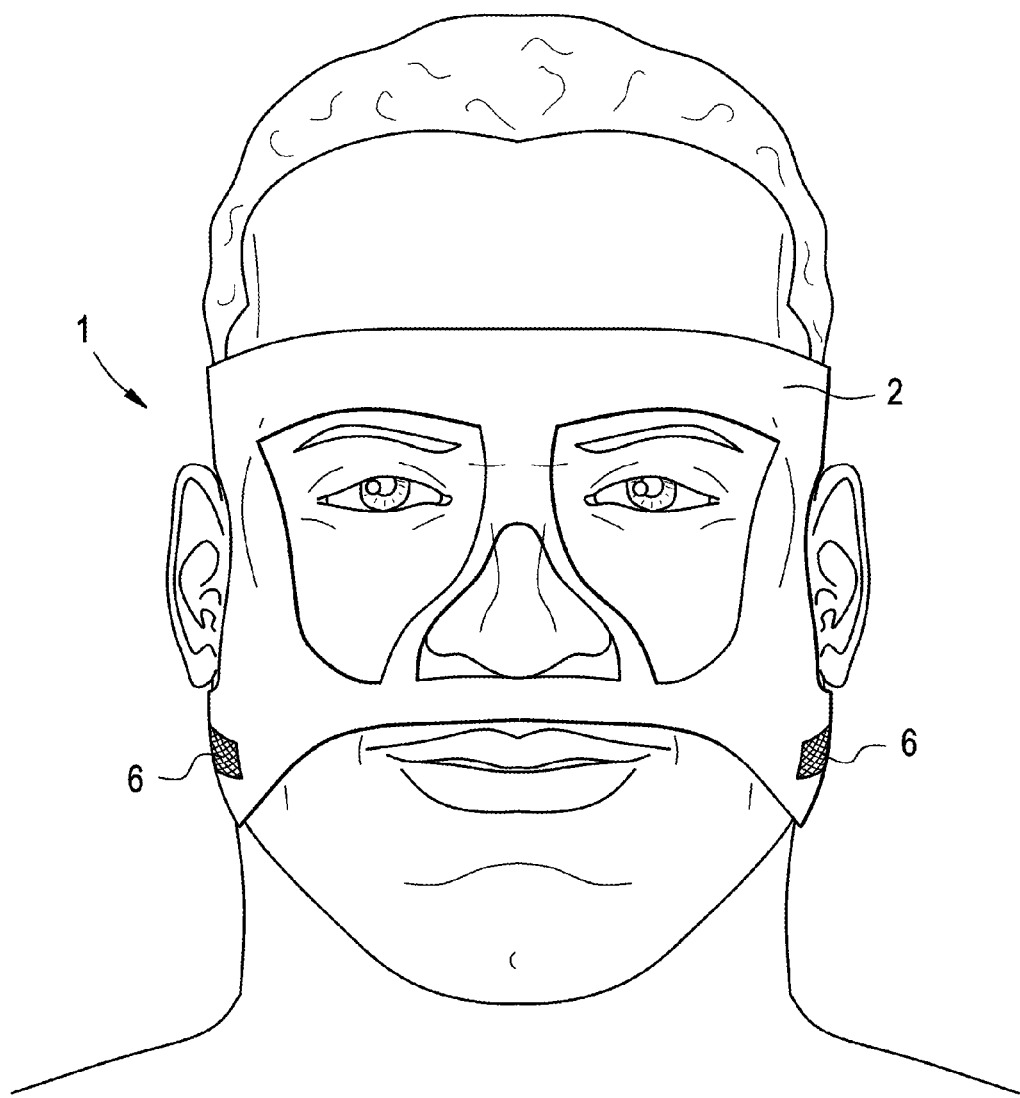
FIG. 1 is a frontal view of the front portion of the wearable airway supporting device that forms a breathable, vision unobstructed face mask portion for a person wearing the device.
Figure 2:
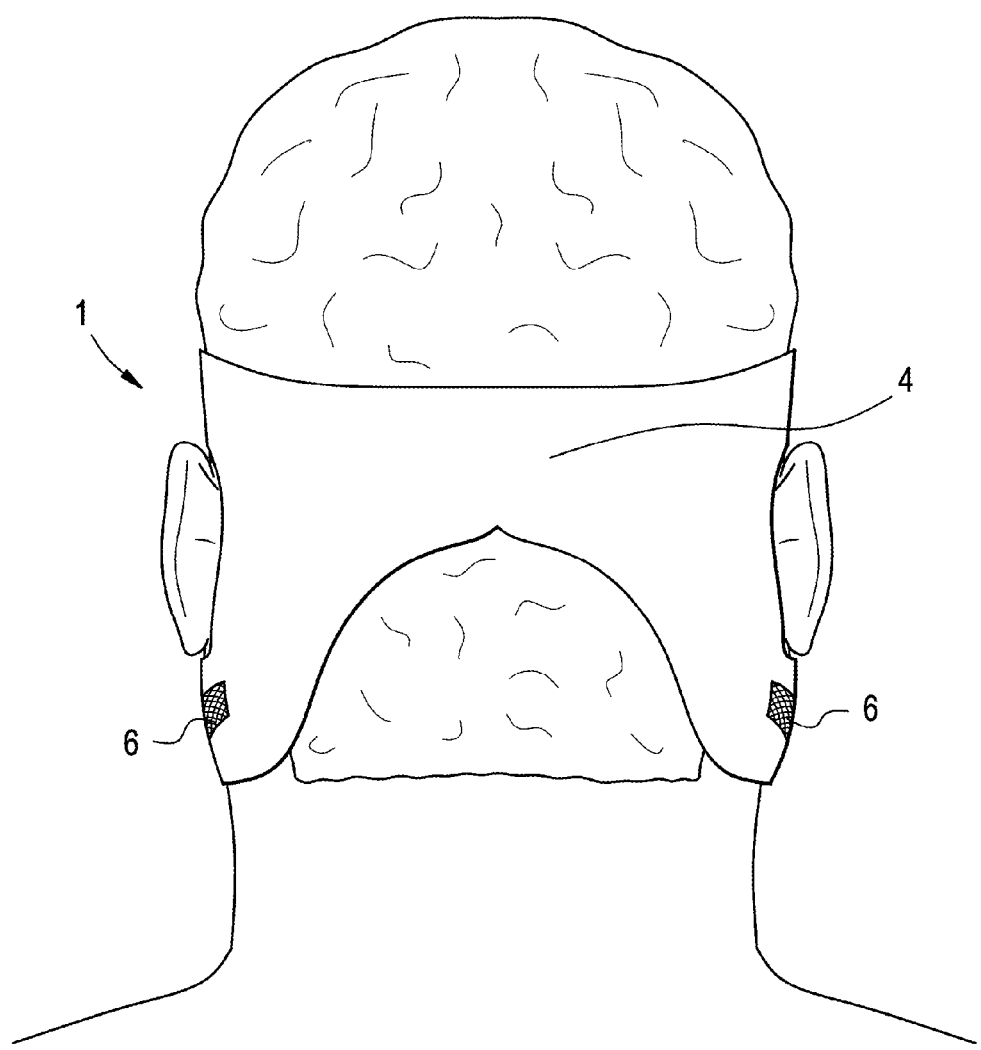
FIG. 2 is frontal view of the rear portion of the wearable airway supporting device that forms a rear head surface covering and has ear openings on a left side and a right side of the rear portion for a person wearing the device.
Figure 3:
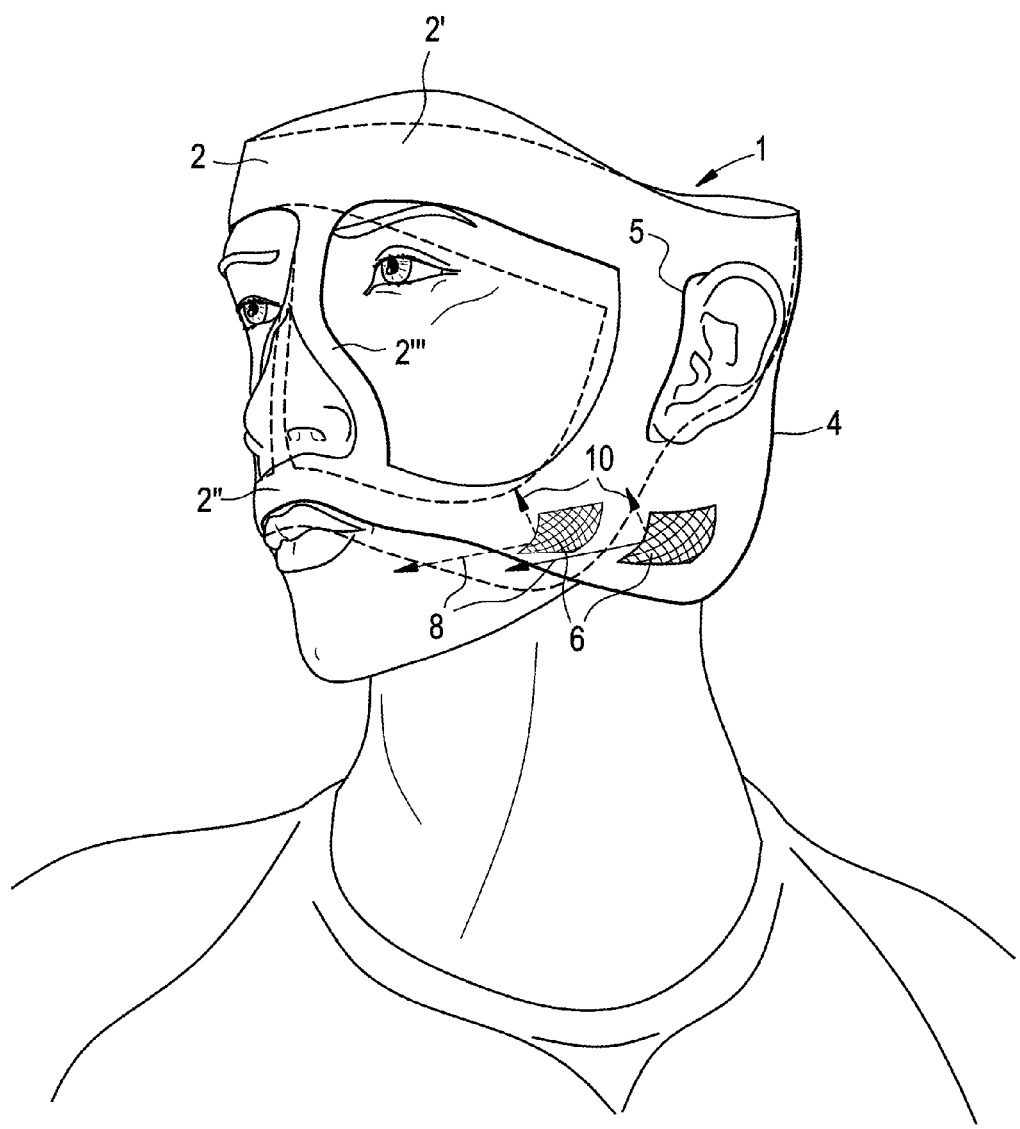
FIG. 3 is an offset side view of one embodiment of the of the wearable airway supporting device with one version of a matching set of form-fit mandible projectors.

The object of the present invention is to effectively support the lower jaw while the user is sleeping or unconscious, and provides the user with an extremely comfortable and desirable jaw supportive device that assists in maintaining an open airway. The wearable airway supporting device has members that encircle the head that, combined with a set of form-fit mandible projectors that exert pressure on at least the pterygoideus internus section of the user's mandible in such a way so as to apply (slightly) upward, primarily outward pressure on the overall lower jaw (mandible) in order to stabilize the mandible while the user is sleeping or unconscious. To this end, the present invention, at its broadest, is directed to a wearable airway supporting device for reducing airway obstruction in humans, wherein the device comprises: (i) an elastic fabric means for holding the lower jaw in an upwardly forward thrust position, wherein the elastic fabric means has at least a front portion and a rear portion, such that the front portion forms a breathable, vision unobstructed face mask portion and the rear portion forms a rear head surface covering and has ear openings on a left side and a right side of the rear portion, and is connected to the front so as to form a single integral member that secures a placement of the device when worn; (ii) a jaw thrust effectuator means formed from a matching set of form-fit mandible projectors or matching jaw thrust effectuator pieces for mandible projection in an upwardly outward direction, the matching set of form-fit mandible projectors being secured to elastic fabric means below and proximate to the ear openings at the left side and a right side of the rear portion. In one embodiment, the wearable airway supporting device is designed so that the front portion includes a forehead band and an upper jaw and lip band, and at least one lateral connecting band therebetween, the at least one lateral connecting band having a nose opening. The matching set of form-fit mandible projectors may be formed from semi-rigid, cushioned materials that provide a requisite firmness sufficient for mandible projection in an upwardly, outward direction, yet can self adjust or be otherwise modified as needed, to diverse shapes and sizes of a human mandible. The elastic fabric means may be formed substantially from fabric made from at least one of the materials chosen from the group comprising polyester, acrylic, polychloroprene (commonly marketed under the trade name Neoprene®), or elastane (commonly marketed under the trade name Spandex®), and may also be provided with anti-bacterial properties that inhibit microbial growth. In an alternative embodiment, the wearable airway supporting device may further include an auxiliary frame for specifically augmenting support and stabilization of the matching set of form-fit mandible projectors, whereby the auxiliary frame is affixed to the matching set of form-fit mandible projectors and is secured to the elastic fabric means. In yet other embodiments, the auxiliary frame for specifically augmenting support and stabilization of the matching set of form-fit mandible projectors can be chosen from the group comprising: an over the head band or a behind the head band, as further described hereafter.

Thus, as seen in FIGS. 1, 2, 3, 4, 5, and 6, inventive device 1 comprises an elastic fabric means which has at least a front portion 2 and a rear portion 4, such that front portion 2 forms a face mask structure or portion that is both breathable and provides for unobstructed vision through cutouts or openings for both the eyes and the nose. Front portion 2 encircles a substantial portion of the user's face, and to that end, includes a forehead band 2' and an upper jaw and lip band 2", and at least one lateral connecting band 2''' therebetween, with at least one lateral connecting band 2''' having a nose opening, and wherein upper jaw and lip band 2" stretches across the user's upper lip back around the user's face to meet rear portion 4, and forehead band 2' covers a portion of the user's forehead and back around the user's face to meet rear portion 4. Rear portion 4 forms a rear head surface covering or structure and has ear openings 5 on a left side and a right side of rear portion 4, and is connected to front portion 2 so as to form a single integral member that secures a placement of the device when pulled over the head in a sleeve-like fashion and worn. It is noted that in an alternative embodiment, rear portion 4 or other parts of the aforementioned elastic fabric means may, instead of having the aforementioned sleeve-like fitting, be provided with a longitudinal cut (not depicted) that allows the elastic fabric means to be wrapped around the head and thereby secured around the head by having the edges of the longitudinal cut re-connected through use of mated hook and loop closure means that are affixed along the longitudinal cut. Such an alternative feature could, in some instances, make device 1 easier to put on and might add more flexibility in order for users to configure the shape and the tension strength/direction toward the form-fit mandible projectors against their individual mandibular angles. In any case, each of the above portions of the inventive device may be formed of various widths and surface area coverages, as long as the overall effect is such that the elastic fabric means provides an inward directed tension to the user's face, neck and head as described below with respect to the interaction therewith of form-fit mandible projectors, also referred to herein as matching jaw thrust effectuator pieces 6. As specifically seen in FIG. 3, a set of matching jaw thrust effectuator pieces 6 are provided within, or affixed to, the elastic fabric means that comprises inventive device 2. As seen for example, in FIG. 3, matching jaw thrust effectuator pieces 6 may be particularly located, in one embodiment, below and proximate to each of ear openings 5 of rear portion 4, with one at the left side of the device/user's head, and one at the right side of the device/user's head.

When provisioned as such, one of the advantages of inventive device 1 over prior art devices such as mouthpieces that sit in a user's mouth is that users can adjust the strength and the direction of matching jaw thrust effectuator pieces 6 themselves. In one embodiment, matching jaw thrust effectuator pieces 6 can be attached and detached from the elastic fabric means that comprises inventive device 2 (and in certain cases, also from/to auxiliary frames 12/12'/12") using a detachable securement means (not specifically depicted), such as a hook and loop material. Unlike prior art approaches, such as mouth pieces which need to be individualized to users by specialists such as dentists or oral surgeons, and which must necessarily remain in the exact position for which they are designed, the users of inventive device 1 can configure the device by setting matching jaw thrust effectuator pieces 6 slightly forward relative to the elastic fabric means that comprises inventive device 1 to gain more tension strength, or slightly backward to loosen it. Matching jaw thrust effectuator pieces 6 can also be set slightly upward or downward relative to the elastic fabric means that comprises inventive device 1 in order to alter the direction of the tension strength. Additionally, matching jaw thrust effectuator pieces 6 can be provided in general forms that fit the pterygoideus internus section of the most users' mandibles, or can even be customized in shape to fit slight differences in bone structure, if needed in special cases. With or without such customization, a user can easily learn how inventive device 1 works best to fit the anatomical features (head size, jaw size, etc.) that vary from person to person, by adjusting the forwards/backwards and upwards/downwards positions matching jaw thrust effectuator pieces 6 slightly forward relative to the elastic fabric means that comprises inventive device 2, thereby maximizing the airway supporting benefit of the device without causing any discomfort by having matching jaw thrust effectuator pieces 6 pushing the user's jaw angle too much. Additionally, it is worth noting that when rear portion forms 4 a rear head surface covering as indicated in the figures described above, it specifically provides for a limited covering of both the neck and back of a users head in such a way as to lend the requisite support of matching jaw thrust effectuator pieces 6 against the pterygoideus internus section of the user, but without impeding the movement of the user, and without creating additional discomfort from undue frictional stress on a user's skin. Specifically, rear portion forms 4 a rear head surface covering that avoids placement below the external occipital protuberance of a user, so that the tension strength toward the mandibular supporters will not be impacted by the user's neck motion. More particularly, when the neck of a user is extended without such inventive structuring of the aforementioned rear head surface covering, this type of normal motion can cause uncomfortable amounts of tension of matching jaw thrust effectuator pieces 6 against the pterygoideus internus section of the user. Conversely, when the neck of a user is flexed without such inventive structuring of the aforementioned rear head surface covering, the tension strength that needs to push matching jaw thrust effectuator pieces 6 forward against the pterygoideus internus section of the user would be lost. Thus, without the inventive structuring of the aforementioned rear head surface covering, users would not be allowed to move their neck, or would suffer from discomfort and/or ineffective jaw thrusting dynamics.

Figure 7:
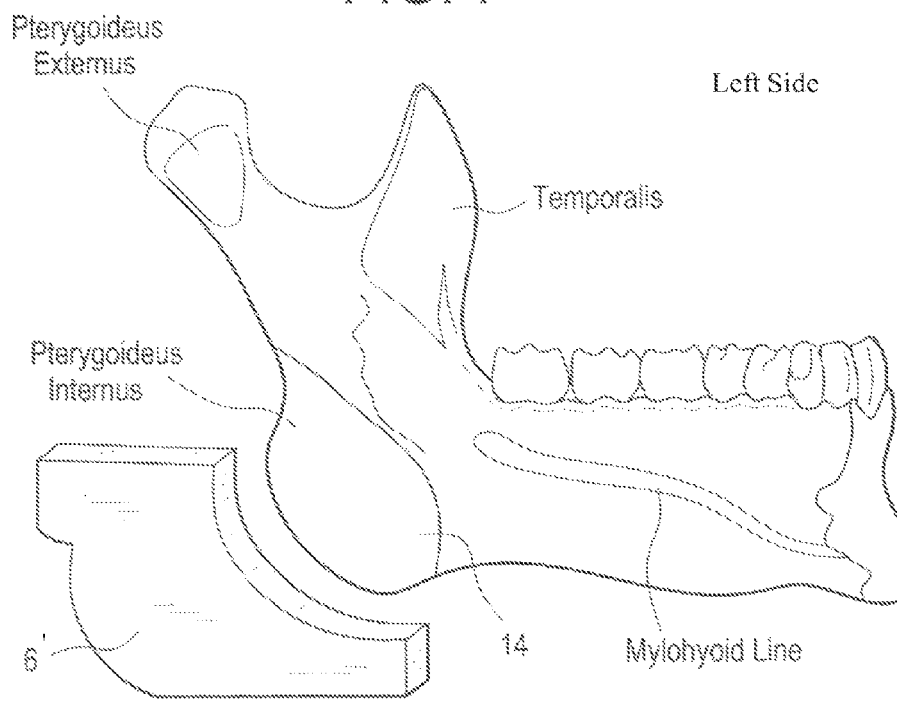
FIG. 7 is a side view of one version of a single form-fit mandible projector from a matching set of form-fit mandible projectors that, when attached to or situated within the elastic fabric means, exerts pressure on at least the pterygoideus internus section of the user's mandible.
Figure 7:
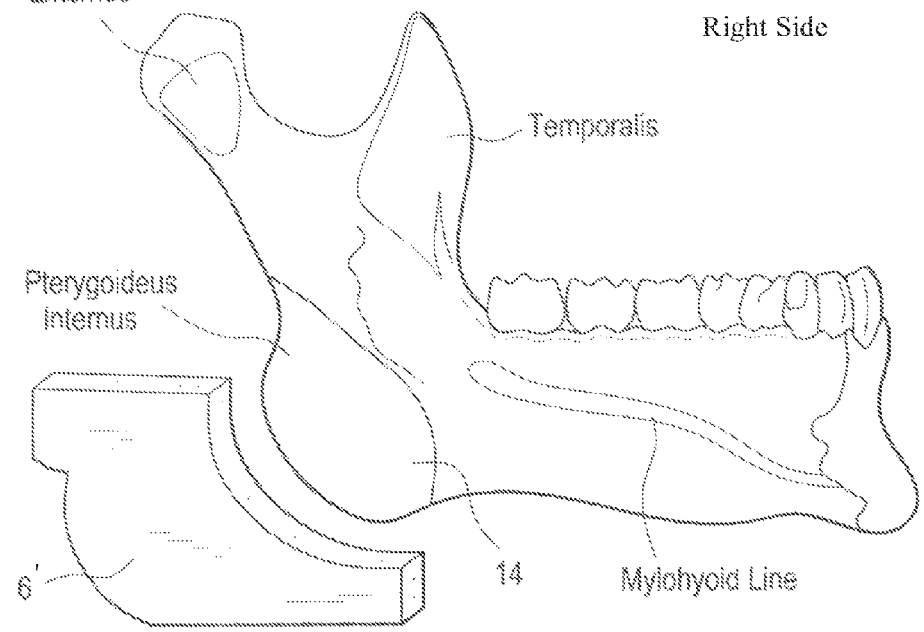

As further seen in FIG. 7, matching jaw thrust effectuator pieces 6' are such that they may be shaped in many different ways, but preferably are directed to discrete formations that are provided with a curvature that can mate up with in a complementary fashion with the curved bone structure of the pterygoideus internus section 14 of a human mandible. Doing so provides both comfort and effective projection of force that is transferred, when inventive device 1 is worn, from the stretched elastic fabric means to each of matching jaw thrust effectuator pieces 6', which in turn, project vectors of force onto the pterygoideus internus section 14 of a human mandible, thereby causing it to jut or be thrust forward (as depicted by force vector 8 in FIG. 3), away from the skull, and to a lesser extent, slightly upwards (as depicted by minor force vector 10 in FIG. 3) at the same time, It is noted that, in order to most effectively accomplish this, matching jaw thrust effectuator pieces 6' should have a certain thickness, perhaps at least approximately ½~¾ inch or so in order to extend far enough out from the user's neckline in order to "catch" enough of the inwardly directed tension of the stretched elastic fabric means. In any case, matching jaw thrust effectuator pieces 6' can be formed from many different materials as long as they are non-toxic and safe to human bodies, such as styrofoam, or any other types of plastic, expanded plastic, polypropylene, polystyrene, etc., so long as the material is selected from a group that is not only inexpensive, durable, and disposable/cleanable, but which has qualities that provide semi-rigid, cushioned materials that provide a requisite firmness sufficient for mandible projection in an upwardly, outward direction, yet can self adjust (e.g., through plasticity or the like) or which be otherwise modified (cut or custom formed or molded) as needed, in order to accommodate the diverse shapes and sizes of human mandibles. In yet one additional embodiment, it may be possible to provide a ready-filled or tillable rubber or plastic sack that is shaped as discussed above, but which can be filled with air, gels, or liquids if desired. When provided in accordance with any of the above variants, the outwardly and slightly upwardly directed force on the lower jaw will have the inevitable anatomic effect of lifting a user's tongue from the posterior pharyngeal wall and opening the user's airway passage during any period of unconsciousness.

Figure 4:
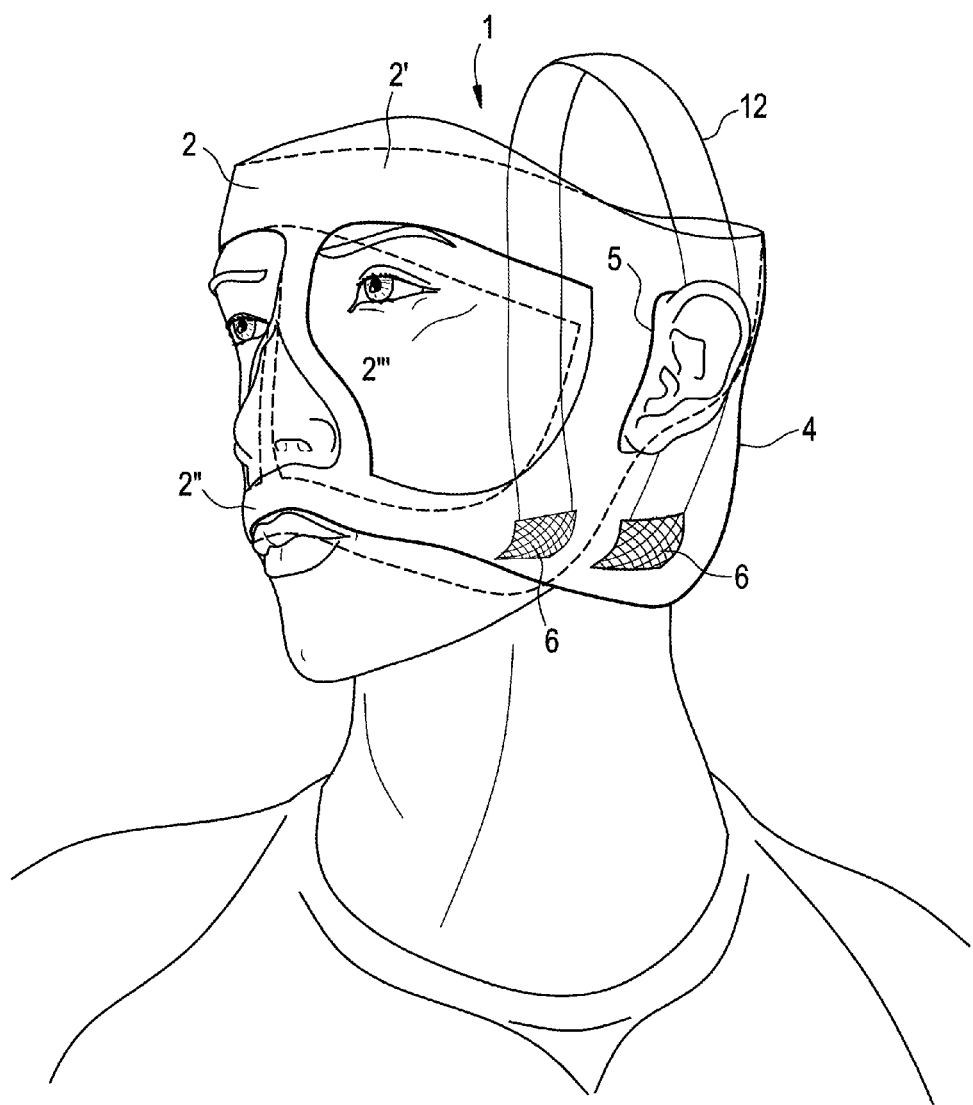
FIG. 4 is an offset side view of one embodiment of the of the wearable airway supporting device utilizing a unified vertical retention brace for retention of a matching set of form-fit mandible projectors.
Figure 5:
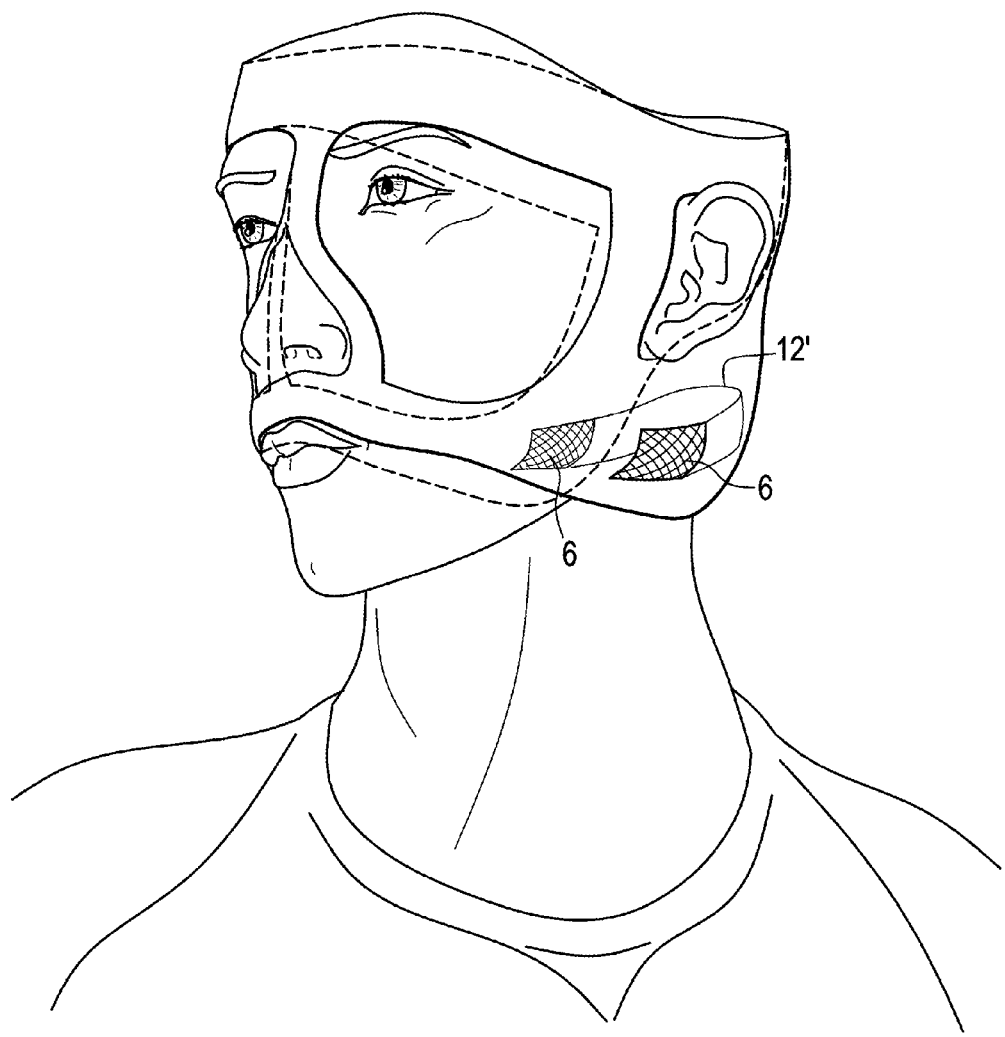
FIG. 5 is an offset side view of one embodiment of the of the wearable airway supporting device utilizing a unified horizontal retention brace for retention of a matching set of form-fit mandible projectors.
Figure 6:
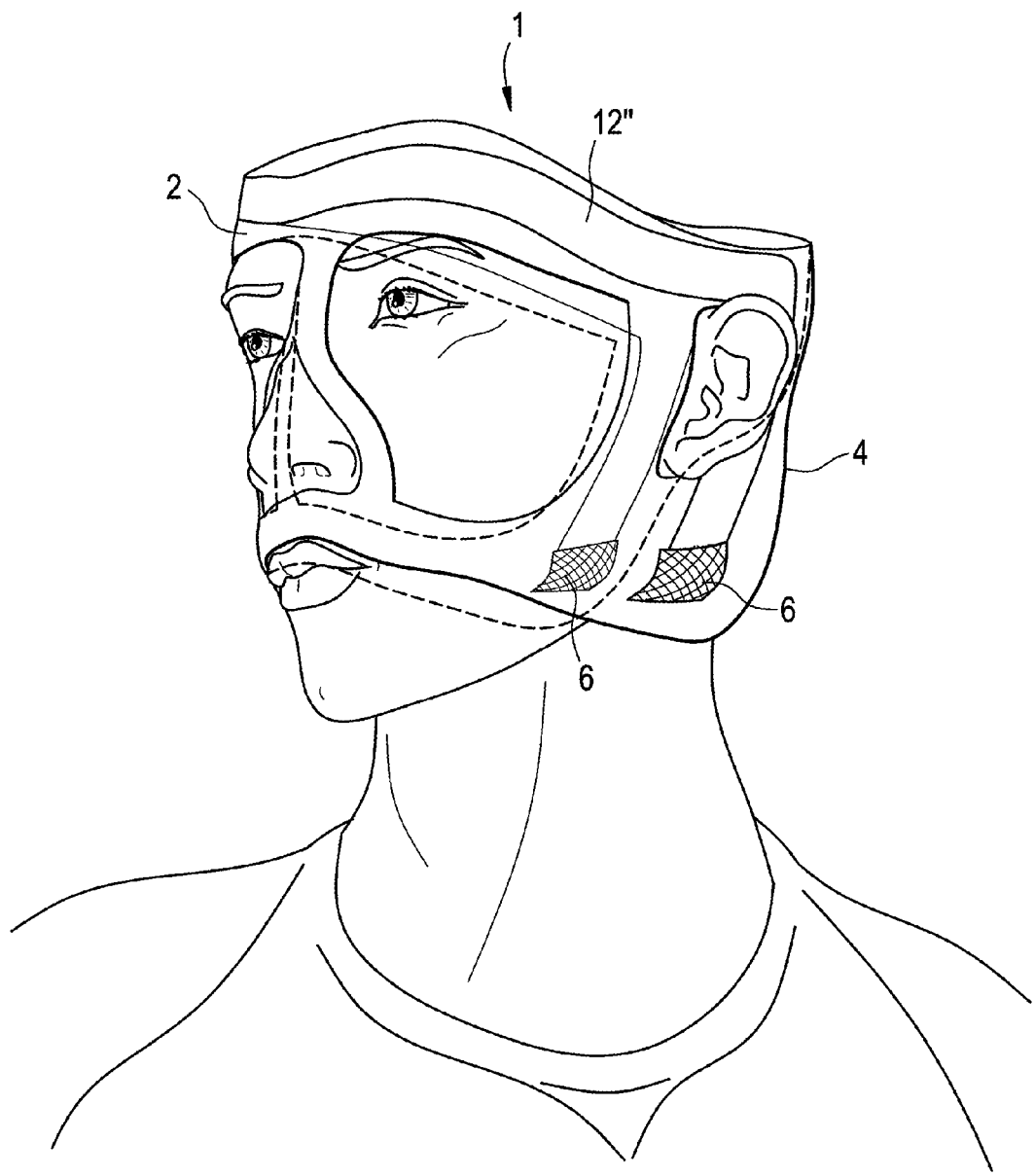
FIG. 6 is an offset side view of one embodiment of the of the wearable airway supporting device utilizing a unified vertical-horizontal retention brace for retention of a matching set of form-fit mandible projectors.

The invention as presented also provides for alternative embodiments regarding the affixment and support of matching jaw thrust effectuator pieces 6. Hence, in an alternative embodiment, the wearable airway supporting device may further include an auxiliary frame 12/12'/12" for specifically augmenting support and stabilization of matching set of form-fit mandible projectors/jaw thrust effectuator pieces 6, whereby the auxiliary frame is affixed to the matching set of form-fit mandible projectors 6 and is secured to, or otherwise retained within a pocket (not specifically depicted) of the elastic fabric means, as seen in FIGS. 4, 5, and 6. In yet other embodiments, the auxiliary frame for specifically augmenting support and stabilization of the matching set of form-fit mandible projectors can be chosen from the group comprising the following structures such as an over the head band 12 (specifically depicted in FIG. 4, and also termed herein as a unified vertical retention brace for retention of matching set of form-fit mandible projectors), a behind the head band 12' (specifically depicted in FIG. 5, and also termed herein as a unified horizontal retention brace for retention of matching set of form-fit mandible projectors), or a forehead band 12" (specifically depicted in FIG. 6, and also termed herein as a unified horizontal-vertical retention brace for retention of matching set of form-fit mandible projectors). In any of the above cases, auxiliary frames 12/12'/12" can provide additional stability to the placement of matching jaw thrust effectuator pieces 6, but also, these frames can further enhance both the retention and force projection of matching jaw thrust effectuator pieces 6, thereby amplifying the outwardly and slightly upwardly directed force on the lower jaw.

It is noted that inventive device 1 may be formed from the above materials so as to not only provide ongoing comfort for users who may require daily wear thereof, but also for hygienic advantages that include the ability to wash inventive device 1, as it is intended to be structurally and materially impervious to washings with water and solvents. Additionally, it may also be possible to impregnate the elastic fabric means with anti-microbial agents such as silver ions or like in order to provide additional protection from microbial growth and the smell associated therewith that arises from ongoing use on the skin. Provision of any or all of the above ensures that it remain odor free when properly taken care of by a user at home. Similarly, for uses in medical treatment facilities, a disposable and/or readily disinfectable embodiment is contemplated that may be disposed after one use, or is amenable to disinfection through standard clinical disinfection approaches such as autoclaves, etc. To this end, a disposable or disinfectable embodiment may be structured as described above, but may utilize cheaper, less long lasting elastic fabric means that may be chosen from materials such as rubber stretch band material or the like, in both standard and hypoallergenic variants. In such a case, matching jaw thrust effectuator pieces 6 may also be disposable, or may be removable for ongoing reuse after the elastic fabric means has worn out or is discarded.

I claim:

1. A wearable airway supporting device for reducing airway obstruction humans, said device comprising:
an elastic fabric means for holding the lower jaw in an upwardly forward thrust position, said elastic fabric means having at least a front portion and a rear portion, wherein the front portion forms a breathable, vision unobstructed face mask portion and the rear portion forms a rear head surface covering, and wherein said rear portion is connected to said front portion so as to form a member that secures a placement of the device when worn;
a matching set of form-fit mandible pieces, said matching set of form-fit mandible pieces effectuating, through a projection of force that is transferred from said elastic fabric means, a mandible projection in an upwardly forward thrust position, said matching set of form-fit mandible pieces having a curvature that is adapted to mate with a curved bone structure of a pterygoideus internus section of a human mandible.

2. The wearable airway supporting device of claim 1, wherein said matching set of form-fit mandible pieces for mandible projection in an upwardly forward thrust position are formed from semi-rigid, cushioned materials that project at least two vectors of force onto a pterygoideus internus section of a human mandible, yet adjusts to diverse shapes and sizes of human mandibles.

3. The wearable airway supporting device of claim 2, wherein said elastic fabric means is formed substantially from fabric made from at least one of materials chosen from the group comprising polyester, acrylic, polychloroprene, or elastane.

4. The wearable airway supporting device of claim 3, wherein said elastic fabric means is impregnated with antimicrobial agents.

5. The wearable airway supporting device of claim 4, wherein said wearable airway supporting device includes an auxiliary frame for specifically augmenting support and stabilization of said matching set of form-fit mandible pieces, said auxiliary frame being affixed to said matching set of form-fit mandible pieces and being secured to said elastic fabric means.

6. The wearable airway supporting device of claim 5, wherein said auxiliary frame for specifically augmenting support and stabilization of said matching set of form-fit mandible pieces is chosen from the group comprising: an over the head band, a forehead band, or a behind the head band.

7. The wearable airway supporting device of claim 6, wherein said rear portion forms a rear head surface covering having a limited covering of an area above an external occipital protuberance of a user that provides support to said matching set of form-fit mandible pieces without impeding a movement when worn, and wherein;
said at least two vectors of force includes a force vector and a minor force vector for mandible projection in an upwardly forward thrust position.

8. The wearable airway supporting device of claim 7, wherein said wearable airway supporting device is configurable for both tension strength and tension direction, wherein said matching set of form-fit mandible pieces are configured to bet set in both forwards and backwards positions relative to said elastic fabric means, and are configured to bet set in both in upwards and downwards positions relative to said elastic fabric means, and wherein; said elastic fabric means is chosen from the group comprising disinfectable and hypoallergenic materials.

* * * * *